(12) United States Patent
Thompson et al.

(10) Patent No.: US 10,041,889 B2
(45) Date of Patent: Aug. 7, 2018

(54) SYSTEM AND METHOD FOR HIGH SPEED SURFACE AND SUBSURFACE FOD AND DEFECT DETECTION

(71) Applicant: The Boeing Company, Chicago, IL (US)

(72) Inventors: Jeffrey G. Thompson, Auburn, WA (US); Morteza Safai, Newcastle, WA (US)

(73) Assignee: The Boeing Company, Chicago, IL (US)

(*) Notice: Subject to any disclaimer, the term of this patent is extended or adjusted under 35 U.S.C. 154(b) by 87 days.

(21) Appl. No.: 15/225,493

(22) Filed: Aug. 1, 2016

(65) Prior Publication Data

US 2018/0031491 A1    Feb. 1, 2018

(51) Int. Cl.
*G01N 21/94* (2006.01)

(52) U.S. Cl.
CPC ................ *G01N 21/94* (2013.01)

(58) Field of Classification Search
CPC ........................................ G01N 21/94
See application file for complete search history.

(56) References Cited

U.S. PATENT DOCUMENTS

| | | | |
|---|---|---|---|
| 7,220,966 B2 * | 5/2007 | Saito | G01N 25/72 250/341.1 |
| 7,287,902 B2 | 10/2007 | Safai et al. | |
| 7,312,454 B2 | 12/2007 | Safai et al. | |
| 7,553,070 B2 * | 6/2009 | Kollgaard | G01N 25/72 250/341.1 |
| 8,167,482 B2 | 5/2012 | Hatcher | |
| 8,204,294 B2 | 6/2012 | Alloo et al. | |
| 8,289,372 B2 | 10/2012 | Hamrelius et al. | |
| 8,498,836 B2 | 7/2013 | Carlson | |

(Continued)

FOREIGN PATENT DOCUMENTS

| | | |
|---|---|---|
| EP | 1391721 A2 | 2/2004 |
| EP | 1392721 A3 | 3/2004 |
| EP | 2823954 A1 | 1/2015 |

OTHER PUBLICATIONS

Berend Denkena et al., "Thermographic online monitoring system for Automated Fiber Placement Processes," Composites, Part B, 2016, pp. 239-243, vol. 97, Elsevier Ltd.

(Continued)

*Primary Examiner* — Casey Bryant
(74) *Attorney, Agent, or Firm* — Economou Silfin LLP; John S. Economou (57) ABSTRACT

A system and method for the detection of foreign object debris materials or defects on and/or under a surface (e.g., outer ply) of a composite part being formed by a composite layup machine. A gantry moves over the composite part along a predetermined length thereof. A thermal excitation source fixed to the gantry directs infrared radiation across the width of the surface of the composite part. A infrared camera fixed to the gantry a predetermined distance away from the thermal excitation source scans the surface as the gantry moves to detect and output scan information thereof. A controller is coupled to the thermal excitation source and to the infrared camera. The controller processes the sequence of infrared images to identify a foreign object debris material or defect located on and/or under the surface.

20 Claims, 5 Drawing Sheets

(56) References Cited

U.S. PATENT DOCUMENTS

| | | | |
|---|---|---|---|
| 8,916,010 B2 * | 12/2014 | Brennan | B29C 70/30 |
| | | | 156/123 |
| 8,986,482 B2 | 3/2015 | McCowin et al. | |
| 9,162,436 B2 | 10/2015 | Nelson et al. | |
| 9,250,134 B2 | 2/2016 | Shepard et al. | |
| 9,839,946 B2 * | 12/2017 | Safai | B08B 5/02 |
| 2006/0043303 A1 * | 3/2006 | Safai | G01N 21/9515 |
| | | | 250/347 |
| 2006/0191622 A1 * | 8/2006 | Ritter | G01N 25/72 |
| | | | 156/64 |
| 2017/0350764 A1 * | 12/2017 | Thompson | G01J 5/10 |

OTHER PUBLICATIONS

European Extended Search Report for EP 17183230.6-1559, dated Nov. 2, 2017.
European Extended Search Report for Ep 17183232.6-1559, dated Nov. 2, 2017.

* cited by examiner

SYSTEM AND METHOD FOR HIGH SPEED SURFACE AND SUBSURFACE FOD AND DEFECT DETECTION

FIELD

This disclosure relates generally to a system and method for high speed surface and subsurface foreign object debris and defect detection, and more particularly for a system and method for detecting surface and subsurface foreign object debris and defects during a composite layup process.

BACKGROUND

Composite materials are increasingly used as substitutes for conventional materials such as aluminum and steel alloys in various structural components due to the generally high strength-to-weight ratio inherent in composite materials. Composite materials may generally be comprised of a network of reinforcing fibers that are generally applied in layers, and a polymeric resin that substantially wets the reinforcing fibers to form an intimate contact between the resin and the reinforcing fibers. High speed composite layup machines are typically used to form each layer. Such machines can lay composite material at a rate of 3000 inches per minute.

A problem can arise, however, when foreign object debris (FOD), contamination or other type of tape layup anomaly is on or within the formed composite part prior to curing. For example, small amounts of entrapped or surface-adhering moisture or other types of contamination can result in delaminating and porosity of the composite material once the curing is completed. In addition, debris such as small pieces of bagging materials, Teflon tapes or breathing material used during the composite layup that becomes entrapped within a composite layer can result in delamination, porosity and wrinkles in the composite part. One particular type of FOD is referred to as a fuzzball and is generated during the manufacture of a composite part formed from layers of carbon fiber reinforced polymer (CFRP) tape. A so-called "fuzzball" consists of strands of CFRP tape that are abraded by contact with the spools holding the tape and which may randomly fall onto the surface of the composite part under manufacture. Further, other types of tape layup anomalies can occur during layup including twists, folds, untacked tows, wrinkles and bridging. FOD and defect detection is currently done manually by visual inspection. Often, however, FODs and defects are either transparent or blend well with a surface color of the composite material and are thus difficult to detect visually. This manual FOD and defect detection method is thus slow and unreliable. Significantly, if the FOD materials and defects are not detected and removed or repaired prior to curing, large and expensive composite parts may be rejected during nondestructive testing.

One-piece composite parts are presently used in many applications, including parts for commercial aircraft. Such parts can be very expensive to manufacture, and very small FOD materials, contamination or defects not removed during the buildup phase of such a part can result in a manufacturing defect that requires the repair or even rejection of the part. The repair or rejection of such parts is thus quite costly and can also result in schedule delays and inventory problems.

Accordingly, there is a need for an automated high-speed inspection system for the detection of surface and subsurface FODs, contamination and defects during the high-speed composite layup process.

SUMMARY

In one aspect, a system is disclosed for the detection of foreign object debris materials or defects on and/or under a surface of a composite part being formed by a composite layup machine. The composite part has a predetermined length and a predetermined width. The system includes a gantry configured to move over the composite part in a first direction along the predetermined length thereof. A first thermal excitation source is fixed to the gantry and is configured to direct infrared radiation across at least a first portion of the width of the surface of the composite part. A first infrared camera is fixed to the gantry a predetermined distance away from the first thermal excitation source and is configured to scan at least the first portion of the width of the surface as the gantry moves over the surface to detect and output scan information of the scanned surface. A controller is coupled to the first thermal excitation source and to the first infrared camera. The controller is configured to process the scan information from the first infrared camera to identify a foreign object debris material or defect located on and/or under the surface.

In a further embodiment, the first thermal excitation source may be configured to direct infrared radiation across the entire width of the surface of the composite part. The first infrared camera may be configured to scan the entire width of the surface as the gantry moves over the surface to detect and output scan information of the scanned surface.

In another further embodiment, the system includes a second thermal excitation source fixed to the gantry and configured to direct infrared radiation across at least a second portion of the width of the surface of the composite part, and a second infrared camera fixed to the gantry a predetermined distance away from the second thermal excitation source and configured to scan at least the second portion of the width of the surface as the gantry moves over the surface to detect and output scan information of the scanned surface. Further, the controller may be coupled to the second excitation source and to the second infrared camera and may be configured to process the scan information from the first and second infrared cameras to identify a foreign object debris material or defects located on and/or under the surface. Still further, the first portion of the width of the surface of the composite part and the second portion of the width of the composite part may be the entire width of the composite part.

In one still further embodiment, the first thermal excitation source and the first infrared camera may be fixed to the gantry via a mechanism for moving laterally along the gantry. In another still further embodiment, the first thermal excitation source and the first infrared camera may be fixed to the gantry via a pivot mechanism.

In another still further embodiment, the gantry may be a parallel member positioned above the composite part being formed in a direction orthogonal to the direction of motion of the gantry. The composite part being formed may be flat or nearly flat. Further, the composite part may be a skin for an aircraft wing.

In an alternative another still further embodiment, the gantry may be an angled member positioned above the composite part being formed in a direction orthogonal to the direction of motion of the gantry. The composite part being formed may have a central flat portion and left and right outer portions angled to the central flat portion, with the first portion being the central flat portion. The system may further include a second thermal excitation source fixed to the gantry and configured to direct infrared radiation across at least a second portion of the width of the surface of the composite part, the second portion corresponding to the left outer portion, a second infrared camera fixed to the gantry a predetermined distance away from the second thermal excitation source and configured to scan at least the second portion of the width of the surface as the gantry moves over the surface to detect and output scan information of the scanned surface, a third thermal excitation source fixed to the gantry and configured to direct infrared radiation across at least a third portion of the width of the surface of the composite part, the third portion corresponding to the right outer portion, and a third infrared camera fixed to the gantry a predetermined distance away from the second thermal excitation source and configured to scan at least the third portion of the width of the surface as the gantry moves over the surface to detect and output scan information of the scanned surface. Further, the controller is coupled to the second excitation source, the second infrared camera, the third excitation source and the third infrared camera and is configured to process the scan information from the first, second and third infrared cameras to identify a foreign object debris material or defect located on and/or under the surface Further, the angled member may have an apex at a central portion thereof, a right end and a left end. In addition, the first excitation source and first infrared camera may be mounted at the apex, the second excitation source and second infrared camera may be mounted at the left end, and the third excitation source and third infrared camera may be mounted at the right end. The composite part being formed may be a spar for an aircraft wing. Further, the left and right outer portions may be orthogonal to the central flat portion.

In yet another still further embodiment, the composite part being formed has a central flat portion and left and right outer portions angled to the central flat portion along the width thereof. The first portion being the central flat portion. The angled member may have an apex at a central portion thereof, a right end and a left end. The first excitation source and first infrared camera may be mounted at the apex. The system also includes a first infrared mirror mounted at the right end of the angled member, and a second infrared mirror mounted at the left end of the angled member. In this embodiment, the first infrared camera has a field of view wider than the central flat portion. The first infrared mirror is mounted to direct a first outer portion of the field of view of the first infrared camera at the right output portion of the composite part and the second infrared mirror is mounted to direct a second outer portion of the field of view of the first infrared camera at the left output portion of the composite part. Further, the composite part being formed may be a spar for an aircraft wing. Still further, the first infrared mirror and second infrared mirror may each be convex.

In a second aspect, a system is disclosed for the detection of foreign object debris material or defects on and/or under an outer ply of a composite part being formed by a composite layup machine. The composite part has a predetermined length and a predetermined width. The composite part has a central flat portion and left and right outer portions angled to the central flat portion along the width thereof. The system includes a gantry configured to move over the composite part in a first direction along the predetermined length of the composite part. The gantry has an angled shape with an apex at a central portion thereof, a right end and a left end. A first thermal excitation source is fixed to the gantry at the apex thereof and is configured to direct infrared radiation across at least the central flat portion of the composite part. A first infrared camera is fixed to the gantry at the apex thereof a predetermined distance away from the first thermal excitation source and is configured to scan at least the central flat portion of the width of the surface as the gantry moves over the surface to detect and output scan information of the scanned surface. A second thermal excitation source is fixed to the gantry at the left end thereof and is configured to direct infrared radiation across at least the left outer portion of the width of the surface of the composite part. A second infrared camera is fixed to the gantry at the right end thereof a predetermined distance away from the second thermal excitation source and is configured to scan at least the left outer portion of the width of the surface as the gantry moves over the surface to detect and output scan information of the scanned surface. A third thermal excitation source is fixed to the gantry at the right end thereof and is configured to direct infrared radiation across at least the right outer portion of the width of the surface of the composite part. A third infrared camera is fixed to the gantry at the right end thereof a predetermined distance away from the second thermal excitation source and is configured to scan at least the right outer portion of the width of the surface as the gantry moves over the surface to detect and output scan information of the scanned surface. Finally, the controller is coupled to the first thermal excitation source, the first infrared camera, the second excitation source, the second infrared camera, the third excitation source and the third infrared camera and is configured to process the scan information from the first, second and third infrared cameras to identify a foreign object debris material or defect located on and/or under the surface.

In a third aspect, a method is disclosed for the detection of foreign object debris materials or defects on and/or under a surface of a workpiece. A gantry having an infrared excitation source and infrared camera mounted in a central portion thereon is moved over a workpiece in a first direction along a length thereof, the infrared camera mounted a predetermined distance away from the thermal excitation source. An infrared radiation beam from the infrared excitation source is directed over the surface of the workpiece as the gantry moves over the workpiece. The surface of the workpiece is scanned with the infrared camera to detect and output scan information of the surface of the workpiece as the gantry moves over the workpiece. The scan information from the infrared camera is processed to identify a foreign object debris material or defect located on and/or under the surface of the workpiece. Further, the infrared camera may be a radiometric camera and the scan information from the infrared camera may be processed to provide temperature information for an upper layer of the workpiece and a subsurface of the workpiece.

In a fourth aspect, a system is disclosed for the detection of foreign object debris materials or defects on and/or under a surface ply of a composite part being formed by a composite layup machine. The composite part has a predetermined length and a predetermined width. A gantry is configured to move over the composite part in a first direction along the predetermined length thereof. The gantry includes a tape layup head and associated infrared heater for forming the surface ply of the composite part. A first infrared camera is fixed to the gantry a predetermined distance away from the infrared heater and is configured to scan the surface ply as the gantry moves over the composite part to detect and output scan information of the scanned surface ply. Finally, a controller is coupled to the first thermal excitation source and to the first infrared camera. The controller is configured to process the scan information from the first infrared camera to identify a foreign object debris material or defect located on and/or under the surface ply.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

U.S. patent application Ser. No. 14/614,198 ("the '198 application"), entitled "System and Method for High Speed FOD Detection," was filed on Feb. 4, 2015 and is assigned to the same assignee and includes the same inventors as this application. The '198 application, which is incorporated by reference herein, describes a FOD detection system which employs a thermal (infrared) excitation source and an associated infrared camera. A controller coupled to the infrared camera is configured to detect FOD on the surface of a composite part under manufacture based on the difference in infrared emitted energy between the composite part and the FOD based on thresholding of a single line of the pixel array of the infrared camera (which is operated in line scan mode) as the thermal (infrared) excitation source and the associated infrared camera move over the surface of the composite part under manufacture.

FOD can also appear under the outer layer (ply) of the composite part under manufacture, but it can be difficult for the system disclosed in the '198 application to identify this type of FOD (i.e., under layer FOD) and surface FOD because of the additional time required for the under layer FOD to absorb energy from the infrared excitation source (based on the thickness of the upper ply and the time necessary for the infrared energy to pass through the upper ply to the FOD thereunder). Because the infrared camera is mounted a fixed distance apart from the thermal (infrared) excitation source, the infrared camera may pass over the under layer FOD before the under layer FOD absorbs enough energy for the required amount of emitted energy for detection. As a result, the system disclosed herein employs an infrared camera that operates in the full two dimensional mode (not line scan mode) at the resolution of the particular camera (e.g., 1024×1024 pixels) and which includes a controller configured to analyze the information generated by the infrared camera to identify under layer and surface FOD (and other types of defects as discussed below) based on differences in thermal emitted energy between the under layer and some types of surface FOD and the composite part under manufacture. Other types of surface FOD may be identified based on reflected infrared energy.

Figure 1A:
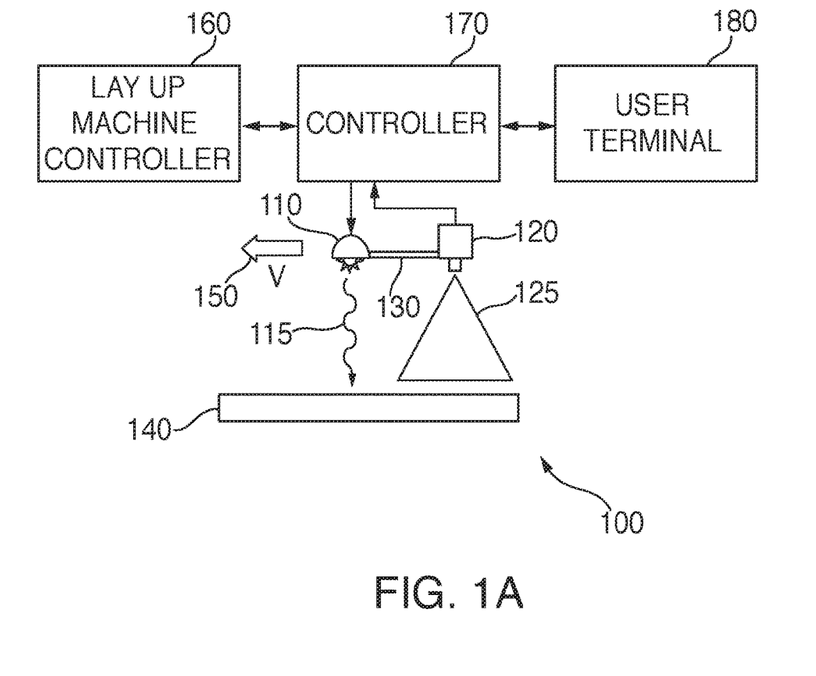
FIG. 1A is a block diagram of a FOD and defect detection system according to the present disclosure and FIG. 1B is a diagram showing FOD detection for surface and under layer FOD using the FOD and defect detection system of the present disclosure.

Referring now to FIG. 1, a system 100 is shown for detecting FOD on the surface of a composite part under manufacture and under, at least, the upper layer of that composite part. System 100 can also identify composite fuzzballs (a particular type of foreign object debris produced during composite part layup) and other types of tape layup anomalies that can occur during layup including twists, folds, untacked tows, wrinkles and bridging. System 100 includes a thermal (infrared) excitation source 110 and an associated infrared camera 120 mounted on a member 130 a fixed predetermined distance apart. Member 130 may be part of an overhead inspection gantry for a composite layup machine, for example. Thermal (infrared) excitation source 110 directs a beam of infrared energy 115 at a workpiece 140 (e.g., a composite part being manufactured). Thermal (infrared) excitation source 110 is mounted a fixed distance above workpiece 140, e.g., twenty feet. Infrared camera 120 scans workpiece 140 and outputs information based on the infrared energy output therefrom for analysis as member 130 is moved over workpiece 140 in a direction shown by arrow 150. Member 130 preferably moves at a fixed rate over workpiece 140. This rate may be as fast as 120 inches/second, and is typically between 50 and 100 inches per second. A controller 170 is coupled to activate thermal (infrared) excitation source 110 (e.g., when a scan of workpiece 140 commences, for example) and to receive the information generated by infrared camera 120. Controller 170 is also linked to a user terminal 180 (which may be a simple status display) and to the layup machine controller 160 to coordinate the operation of system 100 and the movement of member 130 with the operation of the layup machine.

In a further embodiment, infrared camera 120 may be a radiometric infrared camera and controller 170 may be configured to provide real time tape (upper layer) and substrate (inner surface) temperature while member 130 moves over workpiece 140 based on information proved by infrared camera 120.

In an alternative embodiment, member 130 is fixed in position and workpiece 140 is mounted on a movable platform which moves to allow infrared camera 120 to scan the entire length of workpiece 140 as workpiece 140 is moved below member 130.

Figure 1B:
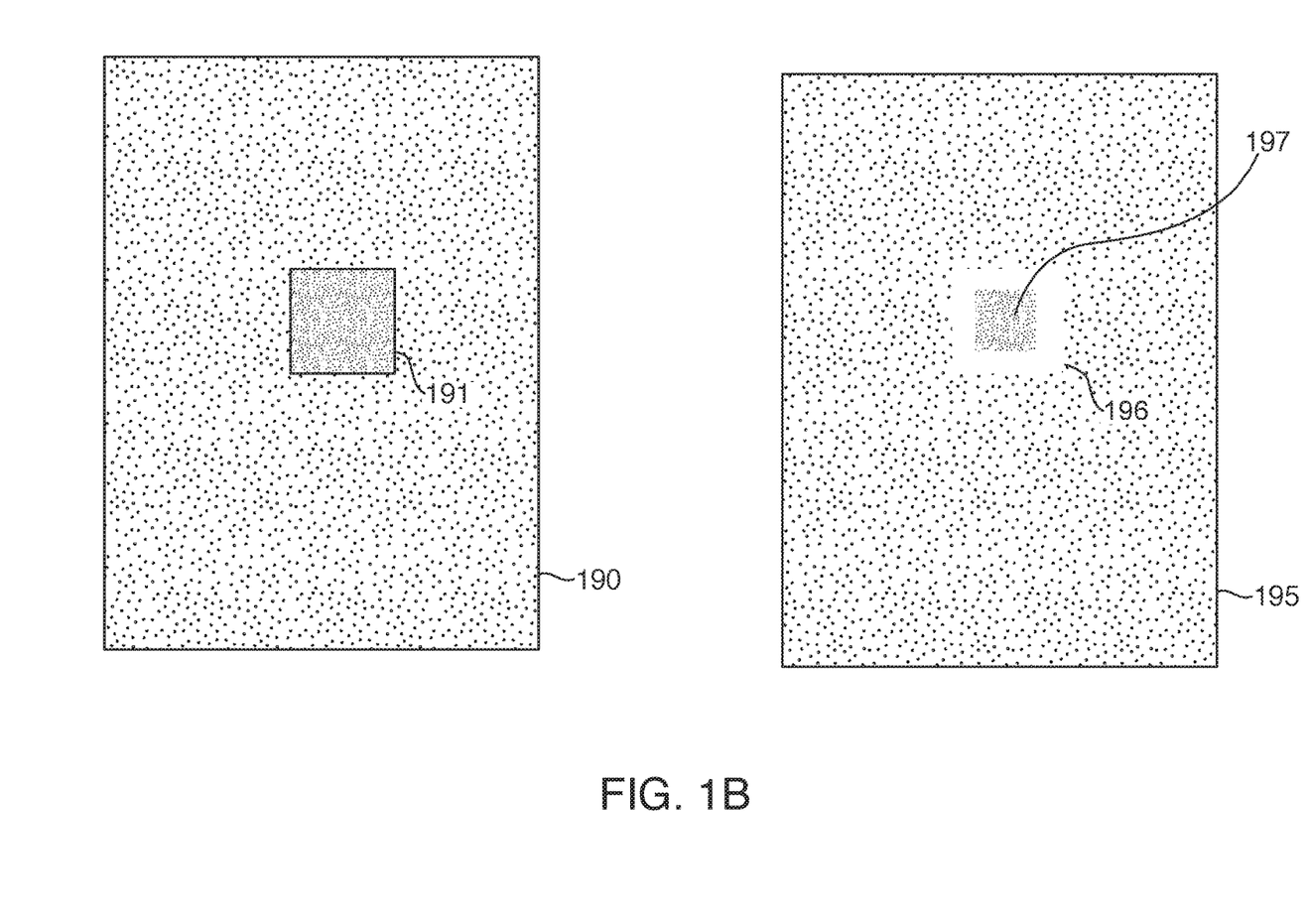

Controller 170 is configured to analyze the information generated by infrared camera 120, and based on differences in thermal emitted energy levels, determine if any under layer and surface FOD or other defects exist. Once an under layer FOD, a surface FOD or other type of defect is found, a message can be provided via user terminal 180 regarding remediation efforts, which may include, for example, removal of surface FOD by hand, the notation of the position of under layer FOD or other defects for later repair, etc. For example, as shown in FIG. 1B, a composite part under manufacture 190 may include a surface FOD 191 that can be identified by the difference in infrared emitted energy between the composite part under manufacture 190 and the surface FOD 191. Similarly, a different composite part under manufacture 195 may include an under layer FOD 197 which may be identified by differences in emitted energy around the border of under layer FOD 197, shown by white area 196. Some other under layer FODs or under layer defects may be identified by having a completely different emitted energy characteristic (not just around the border thereof). Other information may also be derived by controller 170 based on the information from infrared camera 120, including real time measurement of laps and gaps between the laid tape.

Figure 2A:
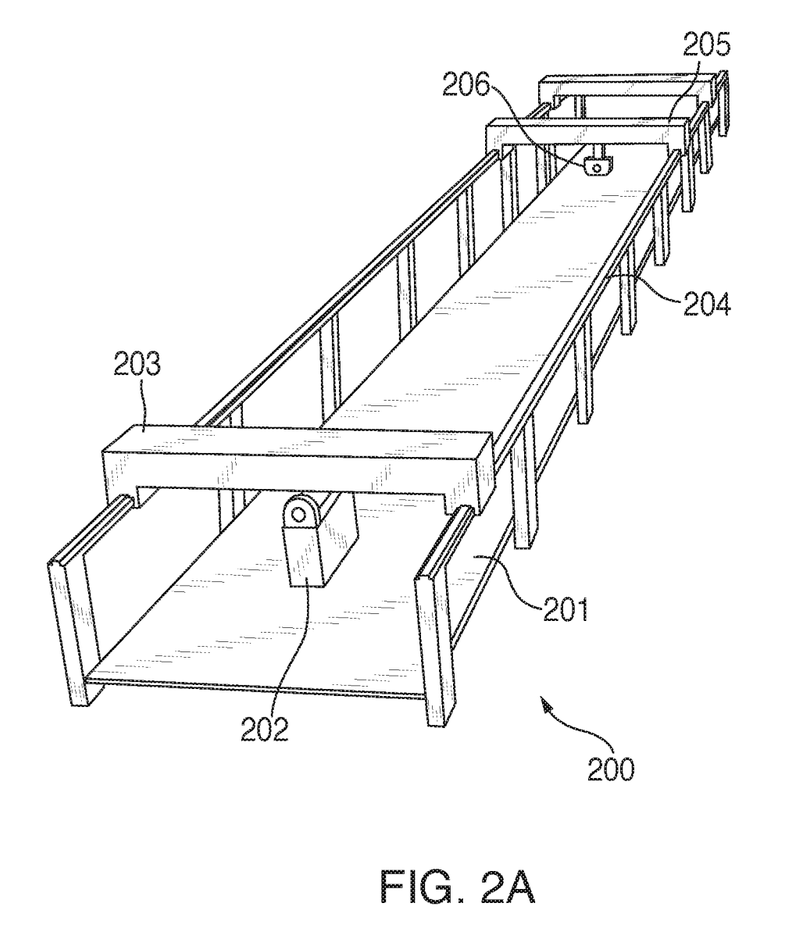
FIG. 2A is a diagram of a lamination cell for forming a carbon fiber wing skin including the FOD and defect detection system of FIG. 1 installed on an inspection gantry according to a first further embodiment the present disclosure.

Referring now to FIG. 2A, a lamination cell 200 for forming a composite part 201 (a workpiece) includes a layup head 202 mounted on a first movable gantry 203 (i.e., a member) that in turn is mounted on a support frame 204. Workpiece 201 includes a length and a width, and gantry 203 is mounted on support frame 204 via a mechanism that allows gantry 203 to move back and forth along the length of workpiece 201 to sequentially add layers of composite material, via layup head 202, to the workpiece during the process of forming the composite part being manufactured. Lamination cell 200 includes a second movable gantry 205 which is also mounted on support frame 204 via a mechanism that allows gantry 205 to move back and forth along the length of workpiece 201. An infrared camera 206 is mounted to gantry 205 along with an associated thermal (infrared) excitation source (not shown in FIG. 2A). Infrared camera 206 and the thermal (infrared) excitation source (not shown) in FIG. 2A correspond to infrared camera 120 and thermal (infrared) excitation source 110 shown in FIG. 1A and operate in an identical manner. In particular, a controller, not shown, is coupled to infrared camera 206 and the thermal (infrared) excitation source. This controller processes the information from infrared camera 206 to identify under layer and surface FOD or other defects in workpiece 201.

Figure 2B:
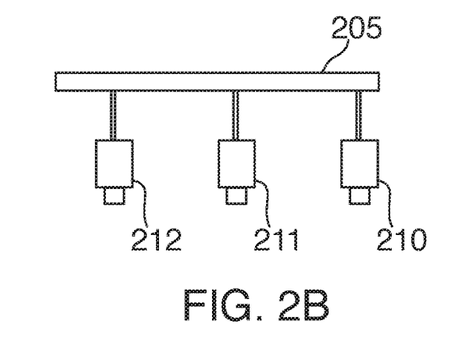
FIG. 2B is a front view of the inspection gantry of FIG. 2A.

Infrared camera 206 in FIG. 2A is mounted on member 205 (an inspection gantry) a fixed distance above workpiece 201, and, based on the particular field of view of infrared camera 206, is capable of examining a particular fixed area of workpiece 201 (the area having a length and width, the length parallel to the direction of movement of member 205). In some cases, the width of the workpiece 201 may be wider than the field of view of infrared camera 206. In such cases, multiple cameras and associated thermal (infrared) excitation sources for each camera may be mounted on the member that moves over the workpiece. For example, as shown in FIG. 2B, an inspection gantry 205 may include three infrared cameras 210, 211, 212 that, taken together, have a field of view wide enough to cover the entire width of the workpiece under examination (the width being perpendicular to the primary direction of movement of inspection gantry 205). The number of cameras employed depends on the width of the workpiece and the field of view of the cameras, and may range from a single camera (and associated thermal excitation source) to four or more cameras (each with an associated thermal excitation source).

Figure 2C:
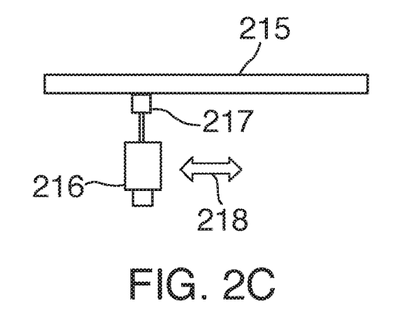
FIG. 2C is a front view of a first alternative inspection gantry.

Alternatively, as shown in FIG. 2C, a single infrared camera 216 may be used that moves laterally (shown by line 218) via a mechanism 217 along the inspection gantry 215 (the associated thermal (infrared) excitation source is not shown but also moves laterally along inspection gantry 215 in coordination with infrared camera 216). In this case, multiple passes can be made over the workpiece, each covering a longitudinal stripe of the workpiece, each stripe overlaying the previous and next stripe.

Figure 2D:
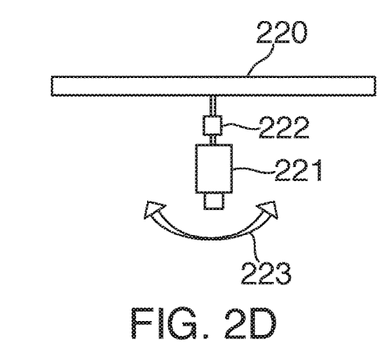
FIG. 2D is a front view of a second alternative inspection gantry.

Finally, as shown in FIG. 2D, a single infrared camera 221 may be used that is mounted to an inspection gantry 220 via a pivot 222 (to allow movement as shown by line 223). In this case, inspection gantry 220 is moved in a stepwise fashion during each lengthwise pass over the workpiece. A pause is inserted at each step to pivot camera 221 back and forth to ensure that the entire width of the workpiece is scanned by infrared camera 221.

Figure 3:
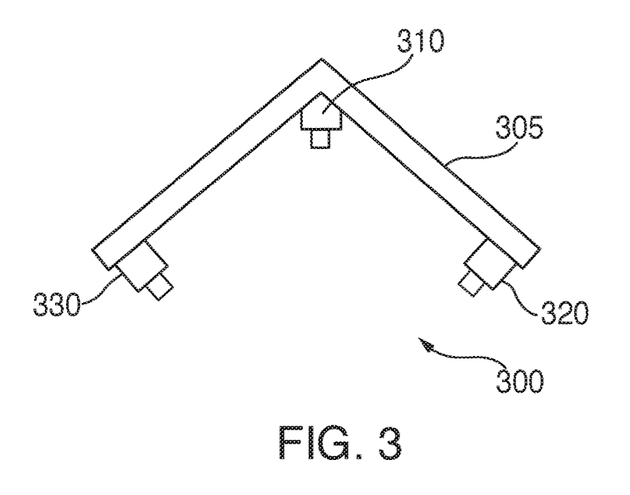
FIG. 3 is a diagram of the FOD and defect detection system of FIG. 1 installed on an inspection gantry for use in a lamination cell for forming a carbon fiber wing spar according to a second further embodiment of the present disclosure.

The system shown in FIG. 2A is effective at scanning a flat or nearly flat workpiece (e.g., a composite wing skin). However, there are many composite parts which are formed that have a surface that is not flat, for example a spar for an airplane wing, but instead includes a top flat portion and side portions orthogonal to the top flat portion. Referring now to FIG. 3, a system 300 for scanning a spar or other non-flat workpiece is shown. In particular, system 300 includes an angled inspection gantry 300 (which replaces the flat inspection gantry 205 shown in FIG. 2A). Three infrared cameras 310, 320, 330 are mounted to inspection gantry 300 (each with an associated thermal (infrared) excitation sources as in FIG. 1 which are not shown in FIG. 3). Infrared camera 310 is mounted at the apex of the angle of inspection gantry 305, and infrared cameras 320, 330 are each mounted at opposite ends of inspection gantry 305. In this manner, infrared camera 310 scans the top flat surface of the workpiece (e.g., spar), infrared camera 310 scans one of the surfaces orthogonal to the top flat surface of the workpiece and infrared camera 330 scans the other of the surfaces orthogonal to the top flat surface of the workpiece. System 300 allows a single pass to inspect a workpiece having a two-dimensional (non-flat) cross section. In some cases the cross-section of the workpiece may have side portions that are orthogonal to the top portion, e.g., in the case of a wing spar, and in other cases the workpiece may include side portions formed at an angle less than ninety degrees to the top portion. System 300 may be used to cover either situation, by adjusting the angle at which each camera 320, 330 is directed at the workpiece.

Figure 4:
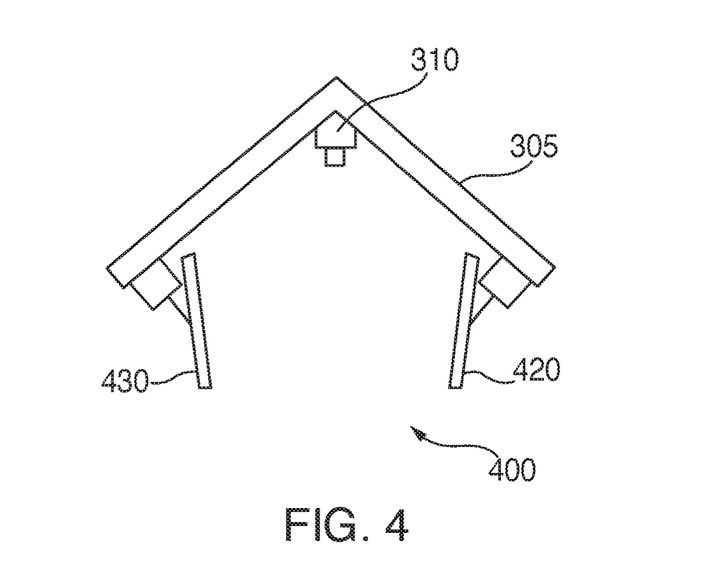
FIG. 4 is a diagram of the FOD and defect detection system of FIG. 1 installed on an inspection gantry for use in a lamination cell for forming a carbon fiber wing spar according to a third further embodiment of the present disclosure.

System 300 in FIG. 3 requires three cameras 310, 320, 330 to scan a non-flat workpiece in a single pass. Referring now to FIG. 4, a system 400 is shown which replaces cameras 320, 330 with infrared mirrors 420, 430. Camera 310 is positioned so that the field of view thereof includes mirrors 420, 430. The angles of mirrors 420, 430 are each adjusted so that the side portions of the non-flat workpiece are within the field of view of camera 310. In this way, system 400 provides significant costs savings over system 300 in FIG. 3 because the infrared mirrors 420, 430 are much less expensive than the two infrared cameras that mirrors 420, 430 have replaced. In a further embodiment, the infrared mirrors 420, 430 may be convex to allow a smaller area mirror to be used and still ensure that the entire portion of the side portions of the non-flat workpiece are within the field of view of camera 310.

In an alternative embodiment, system 100 shown in FIG. 1 may be installed on or adjacent to the tape layup head (e.g., layup head 202 on gantry 203 shown in FIG. 2A) to provide real time monitoring of uncured (green) tape to identify any splits or seams formed in the tape prior to adherence to the substrate. In particular, for lamination heads with low G-forces and adequate mounting space, an infrared camera may be positioned on or adjacent to the tape layup head to take advantage of the infrared heater installed on the lamination head to increase the temperature of the uncured (green) tape as it comes off of the tape creel prior to compaction with the compaction roller to ensure it is sufficiently tacky to adhere to the base substrate—i.e., the top level composite ply laid up in a prior pass of the tape layup head. In this embodiment, the infrared camera may be positioned just behind the compaction roller to monitor the energy emitted from the tape caused by the on-head heater. This embodiment eliminates the need for a separate thermal excitation source as in the prior embodiments.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. A system for the detection of foreign object debris materials or defects on and/or under a surface of a composite part being formed by a composite layup machine, the composite part having a predetermined length and a predetermined width, comprising:
   the composite layup machine configured to form the composite part;
   a gantry positioned over the composite layup machine and configured to move over the composite part in a first direction along the predetermined length thereof;
   a first thermal excitation source fixed to the gantry and configured to direct infrared radiation across at least a first portion of the width of the surface of the composite part;
   a first infrared camera fixed to the gantry a predetermined distance away from the first thermal excitation source and configured to scan at least the first portion of the width of the surface as the gantry moves over the surface to detect and output scan information of the scanned surface; and
   a controller coupled to the first thermal excitation source and to the first infrared camera, the controller configured to process the scan information from the first infrared camera to identify a foreign object debris material or defect located on and/or under the surface.

2. The system of claim 1, wherein the first thermal excitation source is configured to direct infrared radiation across the entire width of the surface of the composite part; and wherein the first infrared camera is configured to scan the entire width of the surface as the gantry moves over the surface to detect and output scan information of the scanned surface.

3. The system of claim 1, further comprising:
   a second thermal excitation source fixed to the gantry and configured to direct infrared radiation across at least a second portion of the width of the surface of the composite part;
   a second infrared camera fixed to the gantry a predetermined distance away from the second thermal excitation source and configured to scan at least the second portion of the width of the surface as the gantry moves over the surface to detect and output scan information of the scanned surface; and
   wherein the controller is coupled to the second excitation source and to the second infrared camera and is configured to process the scan information from the first and second infrared cameras to identify a foreign object debris material or defect located on and/or under the surface.

4. The system of claim 3, wherein the first portion of the width of the surface of the composite part and the second portion of the width of the composite part are the entire width of the composite part.

5. The system of claim 1, wherein the first thermal excitation source and the first infrared camera are fixed to the gantry via a mechanism for moving laterally along the gantry.

6. The system of claim 5, wherein the first thermal excitation source and the first infrared camera are fixed to the gantry via a pivot mechanism.

7. The system of claim 1, wherein the gantry comprises a parallel member positioned above the composite part being formed in a direction orthogonal to the direction of motion of the gantry.

8. The system of claim 7, where the composite part being formed is flat or nearly flat.

9. The system of claim 8, wherein the composite part is a skin for an aircraft wing.

10. The system of claim 1, wherein the gantry comprises an angled member positioned above the composite part being formed in a direction orthogonal to the direction of motion of the gantry.

11. The system of claim 10, wherein the composite part being formed has a central flat portion and left and right outer portions angled to the central flat portion, wherein the first portion is the central flat portion, and further comprising:
   a second thermal excitation source fixed to the gantry and configured to direct infrared radiation across at least a second portion of the width of the surface of the composite part, the second portion corresponding to the left outer portion;
   a second infrared camera fixed to the gantry a predetermined distance away from the second thermal excitation source and configured to scan at least the second portion of the width of the surface as the gantry moves over the surface to detect and output scan information of the scanned surface;
   a third thermal excitation source fixed to the gantry and configured to direct infrared radiation across at least a third portion of the width of the surface of the composite part, the third portion corresponding to the right outer portion;
   a third infrared camera fixed to the gantry a predetermined distance away from the second thermal excitation source and configured to scan at least the third portion of the width of the surface as the gantry moves over the surface to detect and output scan information of the scanned surface; and
   wherein the controller is coupled to the second excitation source, the second infrared camera, the third excitation source and the third infrared camera and is configured to process the scan information from the first, second and third infrared cameras to identify a foreign object debris material or defect located on and/or under the surface.

12. The system of claim 11, wherein the angled member has an apex at a central portion thereof, a right end and a left end, wherein the first excitation source and first infrared camera are mounted at the apex, the second excitation source and second infrared camera are mounted at the left end, and the third excitation source and third infrared camera are mounted at the right end.

13. The system of claim 11, wherein the composite part being formed is a spar for an aircraft wing.

14. The system of claim 11, wherein the left and right outer portions are orthogonal to the central flat portion.

15. A system for the detection of foreign object debris materials or defects on and/or under a surface of a composite part being formed by a composite layup machine, the composite part having a predetermined length and a predetermined width, comprising:
a gantry configured to move over the composite part in a first direction along the predetermined length thereof;
a first thermal excitation source fixed to the gantry and configured to direct infrared radiation across at least a first portion of the width of the surface of the composite part;
a first infrared camera fixed to the gantry a predetermined distance away from the first thermal excitation source and configured to scan at least the first portion of the width of the surface as the gantry moves over the surface to detect and output scan information of the scanned surface; and
a controller coupled to the first thermal excitation source and to the first infrared camera, the controller configured to process the scan information from the first infrared camera to identify a foreign object debris material or defect located on and/or under the surface;
wherein the gantry comprises an angled member positioned above the composite part being formed in a direction orthogonal to the direction of motion of the gantry;
wherein the composite part being formed has a central flat portion and left and right outer portions angled to the central flat portion along the width thereof, wherein the first portion is the central flat portion, wherein the angled member has an apex at a central portion thereof, a right end and a left end, wherein the first excitation source and first infrared camera are mounted at the apex, and further comprising:
a first infrared mirror mounted at the right end of the angled member;
a second infrared mirror mounted at the left end of the angled member; and
wherein the first infrared camera has a field of view wider than the central flat portion, the first infrared mirror mounted to direct a first outer portion of the field of view of the first infrared camera at the right output portion of the composite part and the second infrared mirror mounted to direct a second outer portion of the field of view of the first infrared camera at the left output portion of the composite part.

16. The system of claim 15, wherein the composite part being formed is a spar for an aircraft wing.

17. The system of claim 15, wherein the first infrared mirror and second infrared mirror are each convex.

18. A system for the detection of foreign object debris materials or defects on and/or under an outer ply of a composite part being formed by a composite layup machine, the composite part having a predetermined length and a predetermined width, the composite part having a central flat portion and left and right outer portions angled to the central flat portion along the width thereof, comprising:
the composite layup machine configured to form the composite part;
a gantry positioned over the composite layup machine and configured to move over the composite part in a first direction along the predetermined length of the composite part, the gantry having an angled shape with an apex at a central portion thereof, a right end and a left end;
a first thermal excitation source fixed to the gantry at the apex thereof and configured to direct infrared radiation across at least the central flat portion of the composite part;
a first infrared camera fixed to the gantry at the apex thereof a predetermined distance away from the first thermal excitation source and configured to scan at least the central flat portion of the width of the surface as the gantry moves over the surface to detect and output scan information of the scanned surface;
a second thermal excitation source fixed to the gantry at the left end thereof and configured to direct infrared radiation across at least the left outer portion of the width of the surface of the composite part;
a second infrared camera fixed to the gantry at the right end thereof a predetermined distance away from the second thermal excitation source and configured to scan at least the left outer portion of the width of the surface as the gantry moves over the surface to detect and output scan information of the scanned surface;
a third thermal excitation source fixed to the gantry at the right end thereof and configured to direct infrared radiation across at least the right outer portion of the width of the surface of the composite part;
a third infrared camera fixed to the gantry at the right end thereof a predetermined distance away from the second thermal excitation source and configured to scan at least the right outer portion of the width of the surface as the gantry moves over the surface to detect and output scan information of the scanned surface; and
wherein the controller is coupled to the first thermal excitation source, the first infrared camera, the second excitation source, the second infrared camera, the third excitation source and the third infrared camera and is configured to process the scan information from the first, second and third infrared cameras to identify a foreign object debris material or defect located on and/or under the surface.

19. A method for the detection of foreign object debris materials or defects on and/or under a surface of a workpiece, comprising the steps of:
moving a gantry having an infrared excitation source and infrared camera mounted in a central portion thereon over a workpiece being formed by a composite layup machine in a first direction along a length thereof, the infrared camera mounted a predetermined distance away from the thermal excitation source;
directing an infrared radiation beam from the infrared excitation source over the surface of the workpiece as the gantry moves over the workpiece;
scanning the surface of the workpiece with the infrared camera to detect and output scan information of the surface of the workpiece as the gantry moves over the workpiece; and
processing the scan information from the infrared camera to identify a foreign object debris material or defect located on and/or under the surface of the workpiece.

20. The method of claim 19, wherein the infrared camera is a radiometric camera, further comprising the step of:

processing the scan information from the infrared camera to provide temperature information for an upper layer of the workpiece and a subsurface of the workpiece.

\* \* \* \* \*